(12) United States Patent
Vogt et al.

(10) Patent No.: US 9,144,445 B2
(45) Date of Patent: Sep. 29, 2015

(54) DEVICE AND METHOD FOR DEGASSING AND DISPENSING BONE CEMENT

(75) Inventors: Sebastian Vogt, Erfurt (DE); Tim Schnieber, Frankfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 0 days.

(21) Appl. No.: 13/452,330

(22) Filed: Apr. 20, 2012

(65) Prior Publication Data

US 2012/0285993 A1   Nov. 15, 2012

(30) Foreign Application Priority Data

May 13, 2011   (DE) .......................... 10 2011 101 486

(51) Int. Cl.
*B67D 7/76* (2010.01)
*A61B 17/88* (2006.01)
(52) U.S. Cl.
CPC ......... *A61B 17/8811* (2013.01); *A61B 17/8827* (2013.01)
(58) Field of Classification Search
CPC ................... B65C 17/00503; B65C 17/00516; A61B 17/8827; A61B 17/8811
USPC ........ 222/190, 556–579, 145.5, 146.5, 464.2, 222/499.491–493, 526, 519, 189.09; 206/829, 524.8; 433/89–91
See application file for complete search history.

(56) References Cited

U.S. PATENT DOCUMENTS

| | | | |
|---|---|---|---|
| 558,745 A | | 4/1896 | Sheeby |
| 3,906,958 A | * | 9/1975 | Knox ............................ 604/129 |
| 4,235,344 A | * | 11/1980 | Kulle et al. ................... 215/250 |
| 4,533,068 A | * | 8/1985 | Meierhoefer ............ 222/189.09 |
| 4,671,263 A | | 6/1987 | Draenert |
| 4,758,096 A | | 7/1988 | Gunnarsson |
| 4,973,168 A | | 11/1990 | Chan |
| 5,100,241 A | | 3/1992 | Chan |
| 5,172,807 A | * | 12/1992 | Dragan et al. ................. 206/219 |
| 5,328,262 A | | 7/1994 | Lidgren et al. |
| 5,344,232 A | | 9/1994 | Nelson et al. |
| 5,445,523 A | * | 8/1995 | Fischer et al. ................... 433/90 |
| 5,501,520 A | * | 3/1996 | Lidgren et al. ................. 366/139 |
| 5,551,778 A | | 9/1996 | Hauke et al. |
| 5,586,821 A | | 12/1996 | Bonitati et al. |

(Continued)

FOREIGN PATENT DOCUMENTS

| | | |
|---|---|---|
| DE | 3640279 A1 | 6/1987 |
| DE | 4302230 A1 | 8/1993 |

(Continued)

OTHER PUBLICATIONS

Australian Examination Report Dated Oct. 30, 2012.

(Continued)

*Primary Examiner* — Lien Ngo
(74) *Attorney, Agent, or Firm* — Norris McLaughlin & Marcus PA

(57) ABSTRACT

Device and method for degassing and dispensing bone cement that can be used to produce a bone cement that is largely free of air inclusions. The device contains a dispensing tube (1) that comprises at least one section (2,3) that is permeable to gas, but impermeable to bone cement. The bone cement is being moved along the gas-permeable section which causes the gas present in the bone cement to flow through the gas-permeable material.

6 Claims, 3 Drawing Sheets

(56) References Cited

U.S. PATENT DOCUMENTS

| | | | |
|---|---|---|---|
| 5,624,184 A | 4/1997 | Chan | |
| 6,033,105 A | 3/2000 | Barker et al. | |
| 6,099,307 A * | 8/2000 | Discko, Jr. | 433/90 |
| 6,120,174 A | 9/2000 | Hoag et al. | |
| 6,135,771 A * | 10/2000 | Dragan et al. | 433/90 |
| 6,238,212 B1 * | 5/2001 | Khachatoorian et al. | 433/89 |
| 6,286,670 B1 | 9/2001 | Smith | |
| 6,551,608 B2 | 4/2003 | Yao | |
| 6,682,347 B2 * | 1/2004 | Aoyagi et al. | 433/90 |
| 7,677,418 B2 * | 3/2010 | Henniges et al. | 222/327 |
| 7,748,526 B2 * | 7/2010 | Iwatschenko | 206/219 |
| 2002/0187176 A1 | 12/2002 | Yao | |
| 2002/0191485 A1 | 12/2002 | Jonsson | |
| 2003/0012079 A1 | 1/2003 | Coffeen et al. | |
| 2007/0015106 A1 * | 1/2007 | Bertl et al. | 433/80 |
| 2009/0105366 A1 | 4/2009 | Vogt et al. | |
| 2010/0261139 A1 * | 10/2010 | Leiner et al. | 433/90 |
| 2010/0329074 A1 | 12/2010 | Vogt et al. | |

FOREIGN PATENT DOCUMENTS

| | | | | |
|---|---|---|---|---|
| DE | 60028263 | T2 | 10/2006 | |
| DE | 60126156 | T2 | 10/2007 | |
| DE | 102007050762 | B3 | 5/2009 | |
| DE | 4302230 | C5 | 7/2010 | |
| EP | 0 397 589 | A1 | 11/1990 | |
| EP | 0 692 229 | A1 | 1/1996 | |
| EP | 1 005 901 | A2 | 6/2000 | |
| EP | 1 016 452 | A2 | 7/2000 | |
| EP | 1020167 | A2 | 7/2000 | |
| EP | 2 210 823 | A2 | 7/2010 | |
| SU | 1125261 | * | 11/1984 | 222/190 |
| WO | 94/26403 | | 11/1994 | |
| WO | 99/67015 | | 12/1999 | |
| WO | 2009/032173 | A1 | 3/2009 | |
| WO | 2009/158317 | A1 | 12/2009 | |
| WO | 2009-158317 | A1 | 12/2009 | |

OTHER PUBLICATIONS

Charnley, J.: "Anchorage of the Femoral Head Prosthesis of the Shaft of the Femur", J. Bone Joint Surg., vol. 42, pp. 28-30, 1960.
Breusch S.J. et al.: "Current Status of Cemented Total Hip Arthroplasty in Germany", Z Orthop. vol. 137, pp. 101-107, 1999.
European Search Report of EP 12002634, dated Jul. 10, 2012.
Canadian Office Action Dated May 8, 2013.
Australian Examination Report Dated July 29, 2013.
Austrailian Examination Report Dated Nov. 12, 2013.

* cited by examiner

DEVICE AND METHOD FOR DEGASSING AND DISPENSING BONE CEMENT

The invention relates to a device and a method for degassing and dispensing bone cement.

BACKGROUND OF THE INVENTION

The use of PMMA bone cements is based on the pioneering work of Sir Charnley (Charnley, J.: Anchorage of the femoral head prosthesis of the shaft of the femur. J. Bone Joint Surg. 42 (1960) 28-30.). The structure of PMMA bone cements has remained basically the same ever since. PMMA bone cements consist of a liquid monomer component and a powder component. The monomer component generally contains the monomer, methylmethacrylate, and an activator (N,N-dimethyl-p-toluidine) dissolved therein. The powder component consists of one or more polymers that are made by polymerisation, preferably suspension polymerisation, based on methylmethacrylate and co-monomers, such as styrene, methylacrylate or similar monomers, a radio-opaquer, and the initiator, dibenzoylperoxide. Mixing the powder component and the monomer component, a dough that can be shaped plastically is generated by swelling of the polymers of the powder component in the methylmethacrylate. In this context, the activator, N,N-dimethyl-p-toluidine, reacts with dibenzoylperoxide forming radicals in the process. The radicals thus formed trigger the radical polymerisation of the methylmethacrylate. Upon advancing polymerisation of the methylmethacrylate, the viscosity of the cement dough increases until the cement dough solidifies.

Polymethylmethacrylate bone cements can be mixed by mixing the cement powder and the monomer liquid in suitable mixing beakers with the aid of spatulas. This procedure is disadvantageous in that air inclusions may be present in the cement dough thus formed and cause destabilisation of the bone cement later on. For this reason, it is preferred to mix the bone cement powder and the monomer liquid in vacuum mixing systems. Mixing in a vacuum allows air inclusion to largely be removed from the cement dough and optimal cement quality to thus be attained (Breusch S. J. et al.: Der Stand der Zementiertechnik in Deutschland. Z Orthop. 1999, 137: 101-07). Bone cements mixed in a vacuum have clearly reduced porosity and thus show improved mechanical properties. Various vacuum cementing systems have been described of which only the following shall be named for exemplary purposes: U.S. Pat. No. 6,033,105, U.S. Pat. No. 5,624,184, U.S. Pat. No. 4,671,263, U.S. Pat. No. 4,973,168, U.S. Pat. No. 5,100,241, W99/67015, EP1020167, U.S. Pat. No. 5,586,821, EP1016452, DE3640279, WO94/26403, EP0692229, EP1005901, U.S. Pat. No. 558,745, U.S. Pat. No. 5,344,232.

Aside from removing air or gas inclusions through mixing in vacuo, DE430223005 proposes in addition to also use a vacuum to collect the polymethylmethacrylate bone cement that has been mixed in a vacuum. Said system largely prevents air inclusions in the cement which arise when the polymethylmethacrylate bone cement dough collect at the head end of the cartridges and the remaining residual air between the cement dough and the plunger at the cartridge head is expelled together with the polymethylmethacrylate bone cement dough through the dispensing dispensing tube.

Another concept for attaining a polymethylmethacrylate bone cement that is largely free of air inclusions is used in the Palamix® vacuum cementing system made by Heraeus Medical GmbH, Hanau, that is currently commercially available. In this cementing system, a gas-permeable pore disc is situated in the cartridge head. The air that is present can escape through said pore disc when the polymethylmethacrylate bone cement dough is being dispensed. How-ever, said concept cannot be used with vacuum cementing systems, in which the pore disc is integrated into the plunger.

Aside from the polymethylmethacrylate bone cement that are produced based on powder and liquid, cements made from pastes are also known. According to the invention, the term, polymethylmethacrylate bone cement, includes all production forms of cements, in particular polymethylmethacrylate bone cements made from pastes aside from the cements made from powder and liquid, such as are described, e.g., in DE 102007050762 B3.

It is therefore the object of the invention to provide a simple and safe device and a method for dispensing polymethylmethacrylate bone cements that allow a polymethylmethacrylate bone cement dough that is largely free of air inclusions to be produced.

SUMMARY OF THE INVENTION

The invention provides a device for degassing and dispensing bone cement whose dispensing tube comprises at least one section that is permeable to gas, but impermeable to bone cement.

Preferably, said section is arranged at the back end of the tube, i.e. as closely as possible to the cartridge head.

Surprisingly, it has been found that air inclusions in the bone cement dough are pressed outward during movement along the gas-permeable section due to the application of pressure required for conveying the cement dough through a layer of pores that is arranged in or on the perforated dispensing tube, while the cement dough on the inside of the dispensing tube is simultaneously pressed in the direction of the dispensing opening. A polymethylmethacrylate bone cement that is largely free of air inclusions is obtained at the end of the dispensing tube by this means.

According to the invention, "dispensing tube" shall be understood to mean hollow bodies of different geometries that comprise two openings that are situated opposite from each other. Preferably, this concerns an elongate hollow body that is open on its front and back ends, i.e. at its short sides. The cross-section can be square, multi-angular, oval or round in shape. A hollow body with a round or oval cross-section is preferred. The body can taper towards the dispensing end.

DETAILED DESCRIPTION

The gas-permeable section is preferably formed by a porous filter material. Said filter material must be permeable to gas, but impermeable to the cement dough. The filter material can be provided to be integrated into the dispensing tube. However, it is also feasible that the dispensing tube itself comprises openings that are covered by filter material. Accordingly, for example a sleeve consisting of filter material, at least in sections thereof, can be arranged in the dispensing tube.

If the dispensing tube is conical in shape, the sleeve is provided, for example, as hollow truncated cone such that it is arranged in a press-fit in the dispensing tube and covers openings in the dispensing tube. Owing to the tapering of dispensing tube and sleeve in the direction of the dispensing end, the sleeve is seated fixedly and cannot move along with the polymethylmethacrylate bone cement dough in the direction of the dispensing opening upon pressure being applied to the apparatus.

It is also feasible to provide incisions extending from the back end of the dispensing tube through the thread and up to a certain height. In this case, the sleeve covers the incisions from the inside over their entire height.

Suitable filter materials are sintered porous thermoplastic polyolefins, such as, e.g., polyethylene and polypropylene. The filters can be antimicrobially- or antivirally-equipped. Examples are described in U.S. Pat. No. 6,551,608 B2.

According to the invention, dispensing tube and sleeve may just as well take the shape of a hollow cylinder. In this case, the sleeve should comprise structural elements at the back end that project beyond the circumference. These are then pressed from the back against the rear face of the dispensing tube and thus prevent the sleeve from moving in the direction of the dispensing opening. Said structural elements can be of any shape, for example they can take the shape of a circumferential fin along the outer edge of the sleeve.

The invention also relates to a method for producing a bone cement dough that is largely free of gas inclusions. In this context, the ready-mixed bone cement dough is transported under pressure along a gas-permeable filter surface. Preferably, said method is carried out in a device for degassing bone cement of the type described above.

Surprisingly, air inclusions in the bone cement dough are pressed outward during the movement along the gas-permeable pore layer due to the application of pressure required for conveying the cement dough through a layer of pores that is arranged in or on the perforated dispensing tube, whereas the cement dough remains on the inside of the dispensing tube and is moved in the direction of the dispensing opening of the dispensing tube. This allows a polymethylmethacrylate bone cement that is largely free of air inclusions to be obtained at the end of the dispensing tube.

Accordingly, the present invention can be used to produce a very stable bone cement even without the application of a vacuum.

In the following, preferred embodiments of the invention are described in more detail based on the appended drawings. In the figures,

BRIEF DESCRIPTION OF THE DRAWINGS

FIG. 1 shows a first embodiment of the invention having a dispensing tube 1 that tapers in the direction of the dispensing opening. In the back section, i.e. at the end at which it is to be connected to the mixing device for producing the bone cement dough, openings 2 are provided in the dispensing tube 1. The openings 2 are covered by a sleeve 3. The sleeve 3 consists of a porous filter material that is permeable to gas, but impermeable to the bone cement.

FIG. 2 shows a second embodiment of the invention having a cylindrical dispensing tube 1. As before, the sleeve 3 is cylindrical in shape and is arranged behind the openings 2 that are provided in the dispensing tube. The sleeve 3 comprises at its back end a circumferential projecting fin 4. The fin 4 prevents the sleeve 3 from being shifted along with the bone cement dough in the direction of the dispensing opening.

FIG. 3 shows a third embodiment, in which the porous section 3 of the dispensing tube is provided to be integrated with the dispensing tube.

Figure 1:
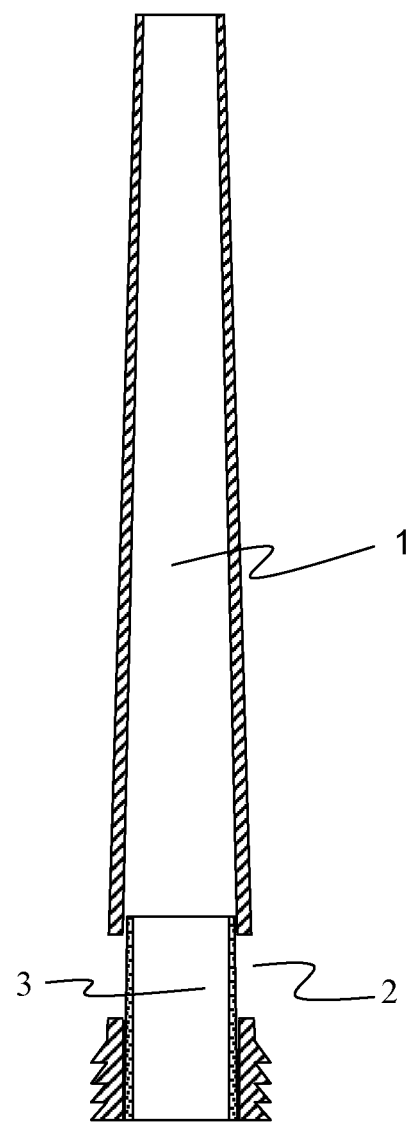
FIG. 1 shows a sectional view of a first embodiment according to the invention.
Figure 2:
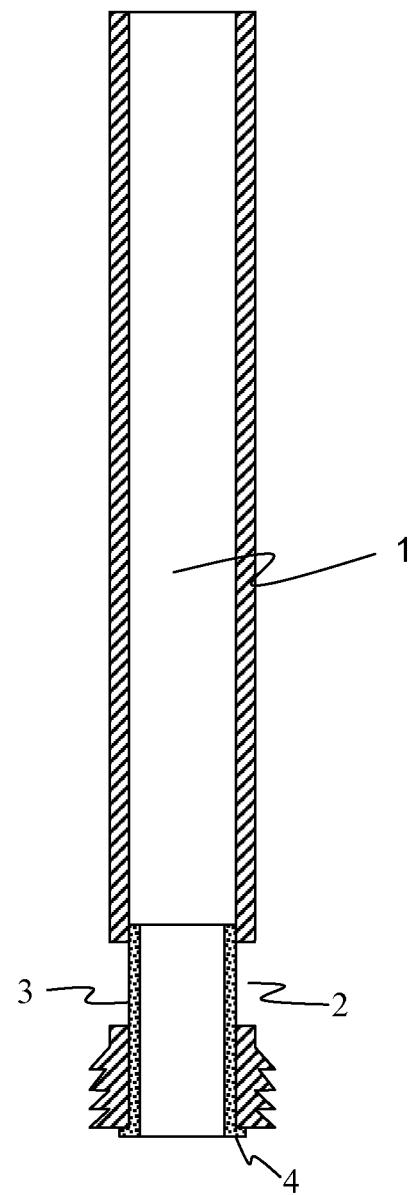
FIG. 2 shows a sectional view of a second embodiment according to the invention.
Figure 3:
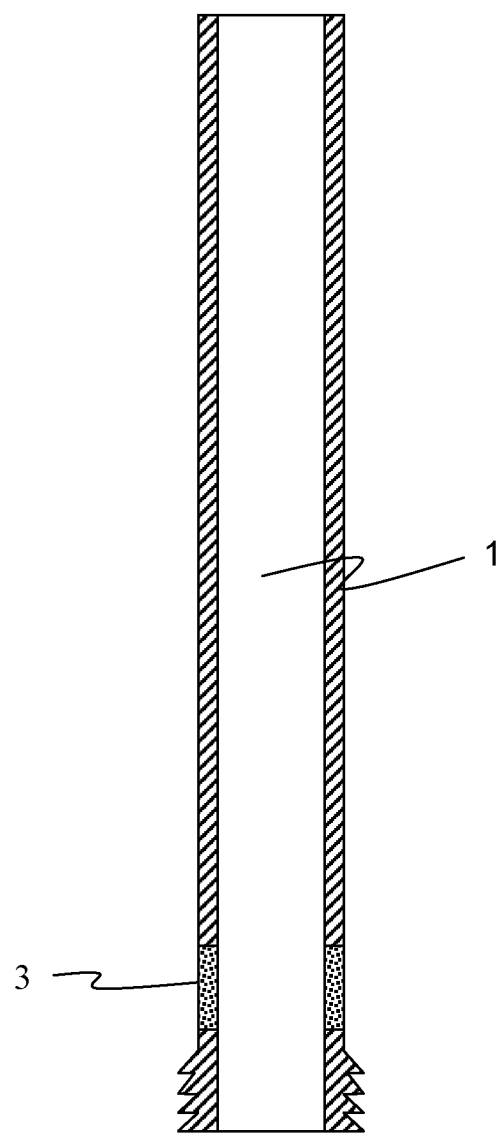
FIG. 3 shows a sectional view of a third embodiment according to the invention.

The invention claimed is:

1. A nozzle formed by an elongate hollow body for degassing and dispensing bone cement from a cartridge containing said bone cement, said elongate hollow body having a wall, at least one section of which is made of a porous material that is permeable to gas but impermeable to bone cement, integrated in the wall and allowing communication of gas directly from the interior of said hollow body through the section of wall that is made of porous material to the ambient.

2. Nozzle according to claim 1, wherein the nozzle is conical in shape.

3. Nozzle according to claim 1, wherein the nozzle is cylindrical in shape.

4. Nozzle according to claim 1, wherein the porous gas-permeable material is a porous filter material.

5. Nozzle according to claim 4, wherein the filter material is a sintered porous thermoplastic polyolefin.

6. Method for degassing and dispensing bone cement, wherein the bone cement is dispensed in a device having a nozzle formed by an elongate hollow body, said elongate hollow body having a wall at least one section of which is made of a porous material that is permeable to gas, but impermeable to bone cement, integrated in the wall, by applying pressure to the bone cement in the dispensing device, whereby the bone cement is moved into and through the nozzle and air inclusions in the bone cement are pressed outward directly through said section of said wall that is made of said gas permeable material to the ambient.

* * * * *